United States Patent
Lehner et al.

(10) Patent No.: US 10,040,753 B2
(45) Date of Patent: Aug. 7, 2018

(54) METHOD FOR PREPARING DIISOCYANATES IN THE GAS PHASE

(71) Applicant: Covestro Deutschland AG, Leverkusen (DE)

(72) Inventors: Peter Lehner, Mülheim an der Ruhr (DE); Rainer Bruns, Bergisch Gladbach (DE); Wolfgang Lorenz, Dormagen (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 15/580,012

(22) PCT Filed: Jun. 7, 2016

(86) PCT No.: PCT/EP2016/062905
§ 371 (c)(1),
(2) Date: Dec. 6, 2017

(87) PCT Pub. No.: WO2016/198404
PCT Pub. Date: Dec. 15, 2016

(65) Prior Publication Data
US 2018/0179149 A1    Jun. 28, 2018

(30) Foreign Application Priority Data
Jun. 12, 2015 (EP) ..................... 15171968

(51) Int. Cl.
*C07C 263/10* (2006.01)
(52) U.S. Cl.
CPC .................. *C07C 263/10* (2013.01)
(58) Field of Classification Search
CPC .................................. C07C 263/10
See application file for complete search history.

(56) References Cited

U.S. PATENT DOCUMENTS

| | | | |
|---|---|---|---|
| 3,226,410 A * | 12/1965 | Hettich | ............ C07C 263/10 422/130 |
| 5,391,683 A | 2/1995 | Joulak et al. | |
| 5,449,818 A | 9/1995 | Biskup et al. | |
| 5,633,396 A | 5/1997 | Bischof et al. | |
| 6,800,781 B2 | 10/2004 | Herold et al. | |
| 6,803,482 B2 | 10/2004 | Jenne et al. | |
| 6,930,199 B2 | 8/2005 | Meyn et al. | |
| 6,974,880 B2 | 12/2005 | Biskup et al. | |
| 7,541,487 B2 | 6/2009 | Pohl et al. | |
| 7,615,662 B2 | 11/2009 | Pohl et al. | |
| 7,754,915 B2 | 7/2010 | Herold et al. | |
| 8,258,337 B2 | 9/2012 | Woelfert et al. | |
| 8,765,996 B2 | 7/2014 | Knoesche et al. | |
| 9,024,057 B2 | 5/2015 | Biskup et al. | |
| 2007/0043233 A1 | 2/2007 | Sanders et al. | |
| 2010/0048942 A1 | 2/2010 | Knoesche et al. | |
| 2017/0210702 A1 * | 7/2017 | Halpaap | ............ C07C 263/10 |

OTHER PUBLICATIONS

Hartung, K.H. et al., Acceleration of turbulent mixture in pipes, Chem Ingenieur Technik, Sep. 1972, vol. 44, Issue 18, p. 1051-1056 (abstract).
Burkholz, A., Droplet Separation, VCH Verlagsgesellschaft, New York, Sep. 1990 (synopsis).
Siemens AG, Pre-Designed Turbo Compressor, Germany, 2013 (brochure).

* cited by examiner

*Primary Examiner* — Paul A Zucker
(74) *Attorney, Agent, or Firm* — Donald R. Palladino

(57) ABSTRACT

Methods for the preparation of diisocyanates by the reaction of the corresponding primary diamines with phosgene in the gas phase are described, wherein the pressure in the diamine evaporation chamber during the transfer of the diamine into the gas phase is less than the pressure in the reaction chamber during the reaction to the diisocyanates, and wherein the pressure difference between the diamine evaporation chamber and the reaction chamber prior to the mixing of diamine and phosgene is overcome by a pressure-increasing element.

13 Claims, No Drawings

METHOD FOR PREPARING DIISOCYANATES IN THE GAS PHASE

CROSS-REFERENCE TO RELATED APPLICATIONS

This application is a national stage application under 35 U.S.C. § 371 of PCT/EP2016/062905, filed Jun. 7, 2016, which claims the benefit of European Application No. 15171968.9, filed Jun. 12, 2015, both of which are being incorporated by reference herein.

FIELD

The invention relates to a method for preparing diisocyanates by reacting the corresponding primary diamines with phosgene in the gas phase, wherein the pressure in the diamine vaporization space during the transfer of the diamine into the gas phase is lower than the pressure in the reaction space during the reaction to form the diisocyanates and the pressure difference between the diamine vaporization space and the reaction space is overcome with a pressure-raising element before mixing of diamine and phosgene.

BACKGROUND

Diisocyanates are produced in large volumes and are mainly used as starting materials to produce polyurethanes. Their preparation usually takes the form of the corresponding diamines being reacted with phosgene. One possible way to prepare diisocyanates is to react the diamines with the phosgene in the gas phase. This form of the reaction, which is typically known as a gas phase phosgenation process, requires the reaction conditions to be chosen such that at least the reaction components diamine, diisocyanate and phosgene, but preferably all the starting materials, assistants, and intermediate and final products of the reaction are gaseous at the chosen conditions. Advantages of gas phase phosgenation include a reduced phosgene hold-up, less by-production, simpler working up to the desired diisocyanate and increased yields for the reaction. The present invention relates solely to gas phase phosgenation.

Various processes for preparing isocyanates by reaction of amines with phosgene in the gas phase are known from the prior art.

EP 0 593 334 B1 discloses a process for preparing aromatic diisocyanates in the gas phase by using a tubular reactor. The walls are constricted to mix the reactants therein. The reaction takes place in the temperature range from 250° C. to 500° C. Yet said process is problematic because reactant stream mixing solely via a narrowing in the tube wall does not work very well by comparison with employing a proper mixing element. Poor mixing typically leads to an undesirably high formation of solids. Ureas for instance may form by dint of a reaction of already formed isocyanate with as yet unconverted starting amine.

There has been no shortage of attempts to minimize this formation of solids, which is especially observable in the reaction of aromatic diamines with phosgene in the gas phase, in order to thereby make possible a gas phase phosgenation of aromatic diamines which is implementable on a large industrial scale. The focus of the improvements in the process for the large scale industrial phosgenation of aromatic diamines in the gas phase is on improving the mixing of the reactant streams and also on homogenizing the flow in the gas phase reactor which lead to a prolonged operating life for the gas phase reactor. In addition to poor mixing of the reactants, an excessive thermal stress on the aromatic diamine also leads to an increased formation of solids, as for instance by ammonia elimination and subsequent formation of ammonium chloride, which specifically at the recovery stage of the phosgene used in excess may come down as a deposit in the corresponding apparatus.

EP 0 570 799 B1 discloses a process for preparing aromatic diisocyanates which is characterized in that the reaction of the related diamine with phosgene is carried out in a tubular reactor above the boiling temperature of the diamine within a mean residence time of 0.5 to 5 seconds, and in which the mean deviation from the mean residence time is less than 6%. Compliance with this contact time is achieved by performing the reaction in a pipe flow regime characterized either by a Reynolds number of above 4000 or a Bodenstein number of above 100. When the pipe flow regime is characterized by a Reynolds number above 4000, the disadvantage is again that, owing to the high rates of fluid velocity needed, the residence time needed for complete conversion of the amines can only be realized in very long mixing and reactor tubes. According to EP 0 570 799 B1, both excessively long and excessively short residence times lead to undesired formation of solids, and therefore the flow in the reaction space has to be homogenized and particularly any backmixing of the components in the reaction space must be foreclosed. EP 0 570 799 B1 discloses that appropriately short mixing times are obtainable using conceptually known methods based on mixing assemblies having moving or static mixing elements, preferably static mixing elements, although, according to EP 0 570 799 B1, it is particularly the application of the jet mixer concept (Chemie-Ing.-Techn. 44 (1972) p. 1055, FIG. 10) which delivers sufficiently short mixing times. EP 0 570 799 B1, however, does not address in any detail the conditions for vaporizing the diamine and the pressure conditions between the vaporization space and the reaction space.

Measures for homogenizing the flow conditions are likewise addressed by EP 1 362 847 B1. EP 1 362 847 B1 discloses a process for preparing aromatic diisocyanates in the gas phase wherein an improved way of performing the reaction in tubular reactors due to fluid-engineering measures such as the homogenization and centerization of the reactant streams serves to avoid temporal variations of the temperature and any asymmetry in the temperature distribution, which are taught by EP 1 362 847 B1 to lead to caking and plugging in the reactor and hence to a shortened operating life for the reactors.

EP 1 449 826 A1 teaches in relation to the reaction of aromatic diamines with phosgene in the gas phase that the reaction of the phosgene with the diamine to form the diisocyanate has to compete against the subsequent reaction of the diisocyanate with the diamine to form the corresponding urea oligomer, and that improved mixing of the starting reactants—phosgene and diamine—coupled with concurrent avoidance of backflow in the tubular reactor enhances the selectivity of diisocyanate formation and reduces urea formation. As a result, so the teaching of EP 1 449 826 A1, it is possible to reduce the amounts of condensation product in the tubular reactor which, owing to their deposition on the reactor wall, lead to a reduction in the clear cross section through the tube and to a gradual increase in the pressure in the reactor and ultimately determine the on-stream time of the process. EP 1 449 826 A1 discloses the use of a so-called multiple nozzle to ensure the improved mixing of the starting reactants, phosgene and diamine. However, EP 1 449 826 A1 does not disclose any details for transferring the diamines into the gaseous state and for the pressure conditions between the vaporization space and the reaction space.

Hardware solutions for improved mixing of the starting reactants are likewise disclosed by EP 1 526 129 A1, DE 103 59 627 A1 and WO 2007/028 715 A1, in that fluid-engineering measures for twist generation (EP 1 526 129 A1 [e]), concentrically disposed annular nozzles with singular (DE 103 59 627 A1 [e]) or multiple amine feeding (WO 2007/028 715 A1) as well as a plurality of amine nozzles disposed parallel to the axis of a tubular reactor (EP 1 449 826 A1) are employed therein.

EP-A-1 526 129 teaches that increased turbulence for the starting reactant stream in the central nozzle has a positive effect on the commixing of said reactants and hence on the gas phase reaction as a whole. The better commixing reduces the proclivity for by-product formation and significantly shortens the required residence time and thus reactor design length.

EP 1 526 129 A1 discloses a shortening of the mixing sector to 42% of its original length on using a spiral helix as turbulency-generating internal fitment in the central nozzle. True, EP 1 526 129 A1 does describe the need for the amine to be vaporized before being sent into the reaction space. Yet since no data whatsoever are disclosed for the corresponding pressure conditions, the notional person skilled in the art is forced to assume that the pressure level is higher in the vaporization space than at the point of entry to the reaction space in order that the desired flow regime may be realized.

But not just the physicotechnical reaction conditions but likewise the properties of the aromatic amines introduced into the reaction with phosgene in the gas phase have been the subject of disclosed processes.

WO 2008/071564 A1 for instance teaches that amines to be converted into the corresponding isocyanates in a gas phase phosgenation have to meet certain requirements. Specifically, the decomposition rate of such amines throughout the duration of the reaction under the prevailing reaction conditions in the gas phase reactor has to be not more than 2 mol %, more preferably not more than 1 mol % and most preferably not more than 0.5 mol %. The aliphatic or cycloaliphatic amines qualify according to WO 2008/071564 A1, but it is also possible to use aromatic amines provided they are transferable into the gas phase without significant decomposition. Directions as to how the aromatic diamines termed suitable can be transferred into the gas phase without significant decomposition or how any decomposition proclivity may at least be reduced, however, are not derivable from WO 2008/071564 A1.

A specific vaporizing technique to limit the thermal stress imposed on the amines used in a gas phase phosgenation is disclosed by EP 1 754 698 A2. EP 1 754 698 A1 teaches that the deposits observed in the reactor for reacting the amines used with phosgene are firstly caused by the amines used decomposing during the reaction. Secondly, long residence times in the vaporization stage and superheating specifically with the use of aliphatic amines lead to the amines used undergoing a partial decomposition by elimination of ammonia. This partial decomposition during vaporization by elimination of ammonia, observed specifically with the use of aliphatic amines, does not just reduce the yield, but in the subsequent phosgenation reaction also leads to deposits of ammonium chloride forming in the downstream pipework and apparatus. The plant equipment then has to be cleaned relatively frequently, giving rise to corresponding production losses. EP 1 754 698 A1 discloses that these disadvantages arise particularly with the tube bundle heat exchangers, plate heat exchangers or falling film vaporizers typically employed for vaporizing and superheating the amines. By way of technical solution, said document discloses preventing the elimination of ammonia during the vaporization by using specific millisized or microsized heat exchangers for vaporizing and superheating aliphatic amines.

One disadvantage with the microsized heat exchangers disclosed in said document EP 1 754 698 A1 is the very small size of their channels, so that even very small amounts of solid material, which are always present in industrial processes, lead to plugging and thereby shorten the on-stream time of the vaporizer. A further disadvantage with the total vaporization disclosed for the amines is that the amines must not contain any nonvaporizable constituents, since these would inevitably form a solid residue on the vaporizer surface, hence impair the heat transfer and finally lead to plugging of the vaporizer. However, providing amines of the required quality in an industrial process is very burdensome and costly. Thus, although the teaching of said document does improve the on-stream time of the reactor, that of the vaporizer is significantly curtailed, so overall the on-stream time of the manufacturing plant is not gainfully improved.

Minimizing the thermal stress for the amines, during their vaporization for reaction with phosgene in the gas phase, is likewise the subject of EP 1 935 876 A1. EP 1 935 876 A1 discloses that the amines, before they are reacted with phosgene, are generally vaporized and heated to 200° C. to 600° C. and, optionally diluted with an inert gas such as $N_2$, He, Ar or with the vapors of an inert solvent, for example aromatic hydrocarbons optionally with halogen substitution, e.g. chlorobenzene or o-dichlorobenzene, are sent to the reaction space. According to said document, the step of vaporizing the starting amines can be effected in any known vaporization apparatus, preference being given to the use of vaporization systems where a small hold-up is circulated at a high rate through a falling film vaporizer while the vaporization process is optionally augmented by injection of inert gas and/or vapors of an inert solvent in order to minimize the thermal stress for the starting amines.

WO 2010/010 135 A1 discloses a process wherein the starting reactants—amine and phosgene—are transferred via an ejector into a mixing zone followed by a diffuser for pressure and temperature increase. This allows vaporization of the amine at a lower pressure than prevailing in the reactor, lowering the boiling temperature of the amine. The disadvantage with this process is that the degree of pressure reduction in the amine vaporizer is greatly dependent on the amine:phosgene ratio and thus on the phosgene excess. A change in the reaction conditions will thus also always have an effect on the pressure in the amine vaporizer and the temperature prevailing there.

SUMMARY

It would be desirable to be able to adjust the amine and phosgene streams largely independently of each other in order to be able to influence the reaction regime and the amine vaporization independently of each other, as is necessary for example in changing the rate of the diamine feedstream to the reactor. More particularly, it would be desirable to have a process management regime whereby the respective inert gas fractions in the starting reactant streams are freely adjustable independently of each other in order, for example, to avoid any unnecessary gas ballast and any burdensome exportation and/or recycling and in order to be able to operate at all times in the most favorable region of fluid flow even under changing rates of diamine feedstreams to the reaction space, the phosgene supply pressure can be kept as low as possible for a given pressure in the reaction space in order to better meet the safety requirements for phosgene handling, and the starting reactant control engineering requirements are kept as simple as possible for cost and availability reasons.

Despite the many attempts to optimize the reaction of amines with phosgene in the gas phase and to minimize the formation of solids which is frequently observed in this connection, therefore, there continues to be a further need to improve the gas phase phosgenation of amines.

Meeting this need, one subject of the present invention provides a process for gas phase phosgenation of primary diamines whereby the transfer into the gas phase of the diamine to be phosgenated is as gentle as possible and very many degrees of freedom are allowed in the choice of process parameters.

The present invention thus more particularly provides a method for preparing a diisocyanate by reacting the corresponding primary diamine with phosgene in the gas phase wherein (i) the primary diamine is transferred into the gas phase at a pressure p1 separately from the phosgene to obtain a gaseous starting material stream A comprising the diamine, (ii) the A starting material stream obtained in (i) is led through a pressure-raising element in which the pressure of starting material stream A is raised to a value $p2>p1$, wherein the pressure difference $p2-p1$ is preferably in the range from 50 mbar to 1500 mbar, (iii) a phosgene-containing gaseous starting material P, which is under the pressure p3, is mixed with the A stream from step (ii) in a mixing device, wherein p3 is preferably greater than or equal to p2, more preferably greater than and most preferably greater by 10 mbar to 100 mbar than p2, and (iv) the mixed stream obtained in (iii) out of said starting material streams A and P is converted in a reaction space at a pressure p4 into the diisocyanate, wherein p4 is preferably less than p2 and less than p3.

DETAILED DESCRIPTION

The term primary diamine is used collectively in the present invention to mean not only aliphatic but also aromatic primary diamines.

All reported pressures are absolute pressures.

Reaction in the gas phase is to be understood as meaning that the diamines are in the gaseous state as they react to form the diisocyanates and that throughout the reaction all the components present (reactants, products, intermediates, any by-products, any inerts) remain not less than 95.0 wt %, preferably not less than 98.0 wt %, more preferably not less than 99.0 wt %, yet more preferably not less than 99.8 wt % and specifically not less than 99.9%, all based on the combined mass of all components present, in the gas phase as they pass through the reaction space.

By reaction space here is meant the space where the preconditions have been established for gas phase reaction of primary diamine (or intermediate products) with phosgene to form the desired diisocyanate. The reaction space thus starts at the point where the gaseous diamine stream and gaseous phosgene stream first meet under conditions that enable a reaction, and ends at the point where either the gas stream consisting of products, by-products, any unconverted reactants and intermediates and also any added inerts is led into a device for liquefying the diisocyanate product (condensing or quenching stage) or the reaction is discontinued by initiating other suitable measures (a sudden reduction in temperature for example). The reaction space is situated in a technical device for conducting chemical reactions, i.e., the reactor. In the simplest case, the reaction space is identical with the inside space of the reactor.

Transfer of the primary diamine into the gas phase is effected in a vaporization space. Said vaporization space is situated inside a technical device for vaporizing liquids, i.e., a vaporizer. In the simplest case, the vaporization space is identical with the inside space of the vaporizer.

Pressure-raising element in the context of this invention refers a technical device for raising a pressure p1 to a value of p2. Pressures in the context of this invention are preferably measured using commercially available pressure transmitters known to the notional person skilled in the art.

The invention will now be explained in detail. Various embodiments of the invention shall be freely combinable with each or one another unless the context clearly suggests otherwise to the notional person skilled in the art.

The process of the present invention preferably uses such primary diamines as are readily transferable into the gas phase without decomposition or where an inherently extant proclivity for decomposition is reducible down to an acceptable degree by employing the method of the present invention. An "acceptable degree" is to be understood in this context as meaning that preferably less than 1 mol %, more preferably less than 0.7 mol % and most preferably less than 0.1 mol % of the primary diamine decomposes in the course of being transferred into the gas phase. Not only aliphatic or cycloaliphatic (i.e., diamines where the amino group(s) is/are bonded to carbon atoms of an aliphatic or cycloaliphatic structure) but also aromatic amines (i.e., amines where the amino group(s) is/are bonded to carbon atoms of an aromatic structure) are suitable for the process of the present invention.

Particularly suitable aliphatic or cycloaliphatic diamines have from 1 to 15 carbon atoms. Preference is given to using 1,6-diaminohexane, 1-amino-3,3,5-trimethyl-5-aminomethylcyclohexane (IPDA) and 4,4'-diaminodicyclohexylamine. 1,6-Diaminohexane (HDA) is used with particular preference.

Particularly suitable aromatic diamines contain one or two aromatic rings. Examples of preferred aromatic diamines are tolylenediamine (TDA), especially 2,4-TDA and 2,6-TDA and mixtures thereof, diaminobenzene (all isomers), naphthyldiamine (NDA, all isomers) and 2,2'-, 2,4'- or 4,4'-methylenediphenyldiamine (MDA) or isomeric mixtures thereof. Particular preference is given to tolylenediamine (TDA), especially 2,4-TDA and 2,6-TDA and mixtures thereof are preferable.

The starting diamines are initially, in the process of the present invention, transferred into the gas phase in a vaporization space (step (i)). This is preferably accomplished using at least one vaporization device as known from the prior art, for example from EP-A-2196455. The diamines are heated to from 180° C. to 600° C., preferably from 190° C. to 500° C., more preferably to from 200° C. to 450° C., optionally diluted with an inert gas such as $N_2$, He, Ar or with the vapors of an inert solvent, for example aromatic hydrocarbons, optionally with halogen substitution, e.g., chlorobenzene or o-dichlorobenzene, and sent to the reaction space. Starting material stream A preferably comprises 99.95 mol % to 75 mol % of the diamine to be phosgenated and from 0.05 mol % to 25 mol % of an inert gas, which is more preferably nitrogen.

In the present invention, the pressure level in the vaporization space for the diamine is equal to a value p1, which is lower than the pressure p2 pressing on the diamine at the point of entry into the mixing device. Said pressure p2 must be not less than the pressure prevailing in the reaction space, the pressure which is hereinafter referred to as p4. Said pressure p4 is preferably measured at the point of entry into the reaction space. Since passage through the mixing device often necessitates the overcoming of any equipment-based pressure difference (the pressure drop across the mixing means), such a case requires p2 (corresponding to the magnitude of the pressure drop across the mixing means) to be made greater than p4. The pressure p1 is preferably from 50 mbar to 1500 mbar, more preferably from 75 mbar to 1400 mbar and most preferably from 100 mbar to 1250 mbar below the pressure p2. This pressure p1, at which the diamine is transferred into the gas phase, is to be understood as meaning the pressure prevailing from the vaporization space to the point of entry into the pressure-raising element. This pressure p1 is preferably measured at the point of entry into the pressure-raising element.

The pressure during the step of transferring the diamine into the gas phase (p1) is preferably in the range from 50 mbar to 1500 mbar. For the purposes of the present invention, the transfer of the diamine into the gas phase may in principle be effected not only at a pressure reduced as compared with standard pressure (1013 mbar) but also at a pressure elevated as compared with standard pressure (1013 mbar). However, the smaller p1 is, the lower the likelihood is of decomposition reactions, and therefore very small pressures p1 are preferable. On the other hand, p1 cannot be made arbitrarily small because the p2–p1 pressure difference to be overcome would otherwise be too large. Therefore, the p1 pressures to be chosen in industrial practice are determined by the specific boundary conditions (type of diamine, type of pressure-raising element, any pressure drop across the mixing means, optimal reaction pressure p4). For TDA as the diamine to be phosgenated, a preferred pressure p1 of 50 mbar to 1500 mbar, more preferably from 75 mbar to 1400 mbar and most preferably from 100 mbar to 1250 mbar will be found advantageous, while the optimal reaction pressure p4 is preferably in the range from 80 to 2500 mbar, more preferably in the range from 120 mbar to 2400 mbar and most preferably in the range from 150 mbar to 2200 mbar.

The transfer of the diamines into the gas phase in a vaporization space may be effected in any vaporizer type known from the prior art. Preference is given to using those vaporizer types where a small hold-up is circulated at a high rate across a falling film vaporizer while in an effort to minimize the thermal stress on the starting diamines the vaporization process—as noted above—is optionally augmented by injection of inert gas and/or vapors of an inert solvent. It may also be preferable to use tube bundle heat exchangers or plate type heat exchangers, optionally with pumped circulation.

A further embodiment of the method according to the present invention may also utilize vaporization apparatus wherein a small hold-up is circulated across at least one microsized heat exchanger or microsized vaporizer. The use of corresponding heat exchangers for the evaporation of diamines is disclosed in EP 1 754 698 A2 for example. For the purposes of this invention it is preferable to use the apparatus disclosed in paragraphs [0007] to [0008] and [0017] to [0039] of EP 1 754 698 A2.

The gaseous diamines may still contain fractions of unvaporized droplets of the diamines, i.e., be in the form of aerosols. Preferably, however, the gaseous diamines contain essentially no droplets of unvaporized diamines. "Essentially" in this context is to be understood as meaning that not more than 0.5 wt % of the diamine, more preferably not more than 0.05 wt % of the diamine, based on the combined mass of the diamine, is in the form of unvaporized droplets while the remainder of the diamine is in gaseous form. It is very particularly preferable for the gaseous diamines not to contain any droplets of unvaporized diamines.

One preferred embodiment includes a step of superheating the gaseous diamine after exit from the vaporizer and before passing through the pressure-raising element. In said superheating step, the temperature of the gaseous diamine on exit from the vaporizer (T1) is raised to a value T11, and this preferably by up to 150° C., more preferably by up to 120° C. and most preferably by up to 90° C. This ensures that the temperature of the gaseous diamine is significantly above its dew point. This stops the gaseous diamine from partly condensing on its way from the vaporizer to the pressure-raising element, inside the pressure-raising element or on its way from the pressure-raising element to the reaction space. Condensation would result in the formation of drops of liquid which are able to lead to caking on the walls or to damage inside to the pressure-raising element. Superheating a diamine which is already in the gaseous state is performable without major risk of decomposition reactions given an appropriately short residence time. Inside the pressure-raising element itself, then, the pressure of the diamine is raised to p2 accompanied by a further rise in the temperature to the value T2, this rise generally being smaller than that from T1 to T11.

Starting diamine vaporization and superheating is preferably further effected in two or more steps in order to prevent unvaporized droplets in the gaseous stream A of starting materials. Preference is given to vaporization and superheating steps where droplet separators are installed between the vaporization and superheating systems and/or the vaporization apparatus also functions as a droplet separator. Suitable droplet separators have been described, for example in "Droplet Separation", A. Bürkholz, VCH Verlagsgesellschaft, Weinheim—New York—Basle—Cambridge, 1989. After leaving the last superheater in the process stream direction, the gaseous stream A of starting materials which has been preheated to its target temperature is sent to the pressure-raising element. After leaving the last superheater in the process stream direction, the gaseous stream A of starting materials which has been preheated to its target temperature is sent to the reaction space for conversion following an average residence time of preferably 0.01 s to 60 s, more preferably of 0.01 s to 30 s and most preferably of 0.01 s to 15 s between exit from the last superheater and entry into the reaction space.

Since the pressure p4 in the reaction space is greater than the pressure p1 in the vaporization space in the present invention, the A stream of starting materials has to pass through a pressure-raising element (step (ii)) for feeding into the reaction space (and first through the mixing device). The pressure-raising element is preferably a compressor. Any device for compressing and conveying process gases which is known to the notional person skilled in the art is conceivable here, examples being piston compressors, screw compressors, rotary piston compressors or turbocompressors. Suitable compressors are for example described in:

"Pre-Designed Turboverdichter (Turbogebläse)", publisher and copyright 2010: Siemens AG, Energy Sector Freyeslebenstraße 1, 91058 Erlangen, Germany. Preference is given to a method wherein the pressure-raising element traversed by said starting material stream A is selected from the group consisting of:
piston compressor, screw compressor, rotary piston compressor and turbocompressor.

The pressure p2 to which the A starting material stream is compressed in the pressure-raising element is preferably in the range from 100 mbar to 3000 mbar, more preferably in the range from 150 mbar to 2800 mbar and most preferably in the range from 200 mbar to 2500 mbar. The p2–p4 pressure difference is preferably in the range from 20 mbar to 800 mbar, more preferably in the range from 20 mbar to 500 mbar, yet more preferably in the range from 30 mbar to 400 mbar and most preferably in the range from 50 mbar to 300 mbar.

The procedure of the present invention—(a) transferring the diamine into the gas phase at a relatively low pressure p1 (and hence at a relatively low temperature), (b) optionally superheating the resultant A stream of starting materials, and (c) compressing the A stream of starting materials to a pressure p2≥p4≥p1—is significantly gentler for the diamine to be phosgenated than the immediate transfer of the diamine into the gas phase at a pressure p2.

To provide the phosgene-containing starting material stream P in step (iii), phosgene is heated at a pressure p3 to temperatures of 200° C. to 600° C. and optionally diluted with inert gas such as $N_2$, He, Ar or with the vapors of an inert solvent, for example aromatic hydrocarbons with or without halogen substitution, e.g., chlorobenzene or o-dichlorobenzene. The aforementioned diluents may also already be present during the heating of the phosgene. The starting material stream P thus obtained, which is under said pressure p3, is sent to the mixing device. The starting material stream P preferably comprises from 99.95 mol % to 75 mol % of phosgene and from 0.05 mol % to 25 mol % of an inert gas or vapors of an inert solvent. An inert gas is used with particular preference and nitrogen is used with very particular preference. The P stream of starting materials is preferably sent to the mixing device without preceding compression. The pressure p3 pressing on the P stream of starting materials is preferably in the range from 100 mbar to 3000 mbar, more preferably from 150 mbar to 2800 mbar and most preferably from 200 mbar to 2500 mbar. The p3–p4 pressure difference is preferably in the range from 20 mbar to 800 mbar, more preferably in the range from 20 mbar to 500 mbar, yet more preferably in the range from 30 mbar to 400 mbar and most preferably in the range from 50 mbar to 300 mbar.

The step of mixing the A and P streams of starting materials in the mixing device is realizable in various ways. Irrespective of how the mixing device is constructed in detail, the risk of renewed dropletization in the mixing step and the further reaction in the reaction space is addressed via technical measures, for example some adequate insulation to avoid radiative heat losses. The mixing device will frequently have an apparatus-based differential pressure $\Delta p_{mixture}$, i.e., p2 and p3 in such a case have to be each at least equal to the combined total of p4 (pressure in the reaction space) and the apparatus-based differential pressure $\Delta p_{mixture}$.

Examples of ways to achieve short mixing times include mixing assemblies or mixing zones having moving or static mixing elements (nozzles for example). Preference is given to static mixers in mixing zones, of the type described for example in EP-B-1 362 847, EP-B-1 526 129 or EP-B-1 555 258 and assigned to the group of smooth jet nozzles and nozzles having turbulency-generating elements. Preference for use in the method of the present invention is given to using the apparatus disclosed in paragraphs [0008] to [0014] and [0023] to [0026] of EP 1362847, that disclosed in paragraphs [0008] to [0013] and [0022] to [0027] of EP 1526129 or that disclosed in paragraphs [0007] to [0011] and [0020] to [0027] of EP-B-1 555 258. Alternatively to the recited mixing assemblies, it is also possible to employ the several nozzles (multiple nozzles) disclosed in EP-A-1 449 826 in sections [0011], [0012] and [0019] to [0027] and arranged in a parallel arrangement with the axis of the tubular reactor.

Particular preference is given to employing reactors having essentially rotationally symmetrical reaction spaces, where the gaseous starting materials, optionally diluted with inerts, are sent to the at least one mixing space in accordance with the jet mixer concept (Chemie-Ing. Techn. 44 (1972) p. 1055, FIG. 10). The injected streams of material preferably enter the at least one mixing space of the reactors at a speed ratio of 2-20, more preferably 3-15, most preferably 4-12. Here it is preferable for the amine, optionally diluted with inerts, to enter the at least one mixing space of the reactors at the higher rate of fluid velocity.

Step (iv) comprises the further reaction in the reaction space of the amine and phosgene mixture obtained in step (iii) to form the diisocyanate. Preferably, neither the reaction space (nor mixing device) has hot surfaces capable of occasioning the occasioning of a thermal stress and consequential secondary reactions such as isocyanurate or carbodiimide formation, nor cold surfaces capable of preferentially occasioning a condensation and the consequential deposition of high-boiling polymeric components. In this way, the reactants phosgene and diamine, apart from the radiative and convective heat losses, are preferably reacted adiabatically (i.e., without technical measures for removing the heat of reaction). In effect, the adiabatic increase in the temperature of the mixing device and in the reaction space is solely established via the temperatures, compositions and relative metering rates of the starting material streams and also the residence time in the mixing device and the reaction space. An isothermal regime for the reaction is also conceivable in principle, yet strict care has to be exercised with removing the heat of reaction in order to prevent any premature condensation.

The residence time in the reaction space is preferably in the range from 0.05 s to 15 s, more preferably from 0.5 s to 5 s. The pressure p4 (the pressure in the reaction space) is preferably in the range from 0.08 bar to 2.5 bar, more preferably from 0.12 bar to 2.4 bar and most preferably from 0.15 bar to 2.2 bar. The reaction is effected at a reactant temperature of preferably 200° C. to 600° C., more preferably 201° C. to 500° C. The gaseous reaction mixture preferably flows through the reaction space essentially without backmixing. This is achieved by the reaction mixture passing through a pressure gradient during its flow through the reaction space (see below for further details).

In one preferred embodiment of the method according to the present invention, the throughput capacity of the employed reactor at the reaction conditions required by the present invention is >1 metric ton of diamine/h, preferably 2-50 metric tons of diamine/h, more preferably 2-18 metric tons of diamine/h. These values apply with particular preference to tolylenediamine, 1,6-diaminohexane and isophoronediamine. Throughput capacity herein is to be understood as meaning that the recited throughput capacity of diamine can be converted in the reactor per hour.

After passage through the reaction space, the reaction is terminated, and this preferably by cooling the reaction mixture down to a temperature at which the diisocyanate product condenses, yet which is still above the decomposition temperature of the corresponding carbamyl chloride.

This may be accomplished, for example, by passing the mixture which departs the reaction space in a continuous manner and which comprises at least diisocyanate, phosgene and hydrogen chloride, after departing the reaction space, to an inert solvent wherein the diisocyanate is dissolved, as already recommended for other gas phase phosgenations (EP 0 749 958 A1).

Preferably, however, the reaction is terminated by the reactor employed in the method of the present invention having at least one zone whereinto one or more suitable streams of liquid ("quench liquids") are sprayed to terminate the reaction of the amines and of the phosgene to the corresponding isocyanates. This, as described in EP 1 403 248 A1, section [0009] to [0019], makes possible rapid cooling of the gas mixtures without employing cold surfaces.

In one particularly preferred form of the present invention, the at least one cooling zone is integrated in a quenching stage as disclosed for example in sections [0014] to [0024], [0032] to [0045] and [0048] of EP 403 248 A1. In one particularly preferred form, two or more cooling zones are employed and these two or more cooling zones are integrated in and operated with a quenching stage as disclosed in EP 1 935 875 A1 as regards constitution and operation.

Instead of the integrated combination of the at least one cooling zone of a reactor with a quenching stage as disclosed in EP 1 935 875 A1, the corresponding integrated combination of the cooling zones of two or more reactors with a quenching stage is likewise possible. However, the integrated combination of a reactor having at least one cooling zone with a quenching stage is preferable.

Irrespective of the method of cooling down chosen, the temperature of the at least one cooling zone is preferably chosen to be above the decomposition temperature of the carbamyl chloride corresponding to the diisocyanate. On the other hand, isocyanate and any solvent co-used as diluent in the gaseous stream of amine and/or gaseous stream of phosgene shall very substantially condense and/or dissolve in the solvent, whereas excess phosgene, hydrogen chloride and any inert gas co-used as diluent very substantially pass through the condensation/quench stage in an uncondensed and/or undissolved state. To selectively recover the diisocyanate from the gaseous reaction mixture, it is particularly suitable to employ solvents such as, for example, chlorobenzene and/or dichlorobenzene maintained at a temperature of 80° C. to 200° C., preferably 80° C. to 180° C., or diisocyanate which is maintained within these temperature ranges or mixtures of diisocyanate with chlorobenzene and/or dichlorobenzene which are maintained within these temperature ranges. It is a simple matter for the notional person skilled in the art to predict which mass fraction of the diisocyanate will condense in the quench and/or pass therethrough without condensing, from the physical data at a given temperature, pressure and composition. It is similarly simple to predict which mass fraction of the excess phosgene, hydrogen chloride and any inert gas used as diluent will pass through the quench without condensing and/or will dissolve in the quenching liquid.

A pressure gradient across the mixing means ensures that the gaseous reaction mixture flows through the reaction space in the manner preferred for the method of the present invention, as a flow without significant backmixing. This pressure gradient across the mixing means is determinatively responsible for the maintenance of a directional flow and of good mixing between the reactants. By contrast, there is no (significant) pressure gradient between the point of exit from the mixing means and the condensation/quenching stage; it is the pressure p4 which prevails here everywhere. The pressures p2 (amine stream A before entry into the mixing device) and p3 (phosgene stream P before entry into the mixing device) are thus both greater than p4, and this at least by the magnitude of the pressure gradient across the mixing means.

The gas mixture departing the condensation/quenching stage is preferably freed from any residual diisocyanate present in a downstream scrub with a suitable scrubbing liquor and thereafter preferably freed from excess phosgene in a conventional manner. This may take the form of a cold trap, absorption in an inert solvent (e.g., chlorobenzene or dichlorobenzene) or of adsorption and hydrolysis on activated carbon. Excess phosgene removed from the gas mixture is preferably returned to the reactor. The hydrogen chloride gas passing through the phosgene-recovering stage may be recycled in a conventional manner to recover the chlorine required for phosgene synthesis. The scrubbing liquor obtained following its use for gas scrubbing is then preferably used in the appropriate zone of the reaction space, at least partly, as a quench liquid to cool down the gas mixture.

Purification of the diisocyanates is preferably effected thereafter by distillative workup of the solutions and/or mixtures from the condensation/quenching stage.

The method of the present invention reduces the thermal stress for the diamine used and hence also its partial decomposition by ammonia elimination. Since the decomposition of the diamine with ammonia elimination leads to the formation of deposits of ammonium chloride, the method of the present invention greatly reduces manufacturing plant fouling. This in turn leads to stabler operation and longer on-stream times. In contradistinction to prior art processes, where a diffuser is employed to raise the pressure and temperature of the reaction mixture after mixing of amine and phosgene, the method of the present invention offers the following advantages:

The inert gas fraction of the starting material streams is independently adjustable across the full range of the diamine flow rates to the reaction space. This avoids an unwanted gas load in the plant and burdensome exportation/recycling, and the reaction space can be operated in whichever is the best fluid flow domain at various diamine flows.

Amount and velocity are independently adjustable for the starting material streams. This reduces control engineering requirements and increases the number of possible parameter variations.

The phosgene pressure upstream of the mixing zone is lower for a given pressure in the reaction zone, since there is no need for a jet effect (as with an ejector). A lower supply pressure ensures better compliance with the safety requirements for phosgene handling.

EXAMPLES

Examples 1 and 2

20.5 kmol/h of a mixture of 2,4- and 2,6-tolylenediamine in a mass ratio of 4:1 are passed into a vaporizer and transferred into the gaseous state. The vaporizer is embodied as a falling film vaporizer with pumped feed and recirculation pump and is operated at a temperature T1 and a pressure p1. The gaseous diamine passes into a first superheater with droplet separator for recycling nonvaporized fractions into the vaporizer. The TDA therein is heated to a temperature T11. The TDA heated to T11 is passed in the next step either into a further superheater where it is heated to T2 (Example 1—comparison) or into a turbocompressor where the pressure of the TDA is raised to p2 and the temperature of the TDA rises to T2 (Example 2—in accordance with the present invention). Thereafter, the amine vapor is passed through a smooth jet nozzle disposed in the reactor axis into the rotationally symmetrical tubular reactor. Concurrently, 123 kmol/h of phosgene are vaporized together with 500 kg/h of ortho-dichlorobenzene and passed at 320° C. at a pressure of 1600 mbar (p3) into the reactor through the annular space surrounding the smooth jet nozzle. The pressure prevailing in the reactor is p4. All the apparatus and pipework from the TDA and phosgene vaporization stage downstream inclusive the reactor are appropriately insulated and where necessary provided a trace heating in order to avoid unwanted condensation or deposits due to heat losses. The reaction reaches an adiabatic end temperature of 405° C. and is complete after 5.5 seconds. The reaction gas mixture is quenched by injection of ortho-dichlorobenzene and the isocyanate formed is condensed and scrubbed and also subsequently worked up by distillation according to known methods.

After 165 days on stream the plant is switched off and opened for cleaning and maintenance.

The table which follows summarizes the experimental parameters and the results:

TABLE

Juxtaposition of Example 1 (comparison) and Example 2 (invention)

| Examples | p1/ mbar | p2/ mbar | p3/ mbar | p4/ mbar | T1/° C. | T11/° C. | T2/° C. | Yield of TDI/ % of theory [1] | State of plant after 165 d |
|---|---|---|---|---|---|---|---|---|---|
| 1 (comp.) | 1600 | — | 1600 | 1540 | 306 | 330 | 395 | 95.5 | [2] |
| 2 | 800 | 1600 | 1600 | 1555 | 278 | 360 | 395 | 95.7 | [3] |

[1] The computed yield is based on the conversion of the starting TDA into TDI in the crude product (liquid phase after quench).
[2] The inside wall of the reactor in the region of the condensation stage (quench) is found to contain, underneath the quench nozzles and in the collector for the crude isocyanate product after quenching, caking and deposits that are attributable to increased by-production. The region for working up the gas mixture departing the condensation stage is found to contain, inside apparatus and pipework, solid deposits consisting predominantly of ammonium chloride. The areas concerned are mostly surfaces having lower temperatures, which favor a condensation of solid ammonium chloride from the gas phase. Ammonium chloride is formed from ammonia and hydrogen chloride in the gas phase phosgenation following thermal decomposition of the starting amine. These ammonium chloride deposits increase the pressure drop across the plant, lead to an impairment of heat transfers and also to an impairment of mass transfer areas on corresponding internal fitments.
[3] The inside wall and collector for the crude isocyanate product downstream of the quench are substantially free of deposits. Nor are any significant deposits found in the region where the crude isocyanate mixture is worked up and where the gas mixture departs the condensation stage.

Accordingly, the procedure of the present invention leads to an avoidance of undesirable deposits and a somewhat increased yield.

What is claimed is:

1. A method for preparing a diisocyanate by reacting the corresponding primary diamine with phosgene in the gas phase comprising:
   (i) transferring the primary diamine into the gas phase at a pressure p1 separately from the phosgene to obtain a gaseous starting material stream A comprising the diamine,
   (ii) leading the A starting material stream obtained in (i), optionally after superheating, through a pressure-raising element in which the pressure of starting material stream A is raised to a value p2>p1,
   (iii) mixing a phosgene-containing gaseous starting material P with the A stream from step (ii) in a mixing device, and
   (iv) converting the mixed stream obtained in (iii) in a reaction space into the diisocyanate.

2. The method of claim 1 wherein the pressure-raising element is selected from the group consisting of:
   a piston compressor, a screw compressor, a rotary piston compressor and a turbocompressor.

3. The method of claim 1 wherein the mixing device is a static mixing device.

4. The method of claim 3 wherein the static mixing device is selected from the group consisting of:
   a smooth jet nozzle and a nozzle incorporating turbulency-generating elements.

5. The method of claim 1 wherein p2 is 50 mbar to 1500 mbar greater than p1.

6. The method of claim 1 wherein the phosgene-containing gaseous starting material stream P is, on entry into the mixing device, under a pressure p3 which is greater than or equal to p2.

7. The method of claim 6 wherein p3 is up to 100 mbar greater than p2.

8. The method of claim 6 comprising effecting the reaction in step (iv) at a pressure p4 which is less than p2 and less than p3.

9. The method of claim 8 wherein the pressure differences p3–p4 and p2–p4 each independently range from 20 mbar to 800 mbar.

10. The method of claim 1 further comprising working up the diisocyanate obtained in step (iv) to purified diisocyanate by further steps comprising a distillation.

11. The method of claim 9, wherein the pressure differences p3–p4 and p2–p4 each independently range from 20 mbar to 500 mbar.

12. The method of claim 11, wherein the pressure differences p3–p4 and p2–p4 each independently range from 30 mbar to 400 mbar.

13. The method of claim 12, wherein the pressure differences p3–p4 and p2–p4 each independently range from 50 mbar to 300 mbar.

* * * * *